US005681333A

United States Patent [19]
Burkhart et al.

[11] Patent Number: 5,681,333
[45] Date of Patent: Oct. 28, 1997

[54] METHOD AND APPARATUS FOR ARTHROSCOPIC ROTATOR CUFF REPAIR UTILIZING BONE TUNNELS FOR SUTURE ATTACHMENT

[75] Inventors: Stephen S. Burkhart, San Antonio, Tex.; Donald K. Shuler, Naples, Fla.

[73] Assignee: Arthrex, Inc., Naples, Fla.

[21] Appl. No.: 555,335

[22] Filed: Nov. 8, 1995

[51] Int. Cl.⁶ ................................... A61B 17/00
[52] U.S. Cl. ................. 606/148; 606/96; 606/104; 128/898
[58] Field of Search ............... 606/96–98, 102–104, 606/86–88, 139, 148, 232; 128/898

[56] References Cited

U.S. PATENT DOCUMENTS

| 4,622,960 | 11/1986 | Tam | 606/103 |
|---|---|---|---|
| 5,250,055 | 10/1993 | Moore et al. | 606/148 |
| 5,330,468 | 7/1994 | Burkhart | 606/96 |
| 5,387,227 | 2/1995 | Grice | 606/222 |
| 5,575,801 | 11/1996 | Habermeyer et al. | 606/232 |
| 5,584,839 | 12/1996 | Gieringer | 606/96 |

OTHER PUBLICATIONS

S.J. Snyder, M.D., "The Revo Rotator Cuff Fixation System," Linvatec Corporation, 1993.

*Primary Examiner*—Jeffrey A. Schmidt
*Attorney, Agent, or Firm*—Ostrolenk, Faber, Gerb & Soffen LLP

[57] ABSTRACT

A straight, cannulated drill guide having a slidable aiming arm is used to align a multi-functional drillhook for drilling a tunnel in the proximal humerus. The drillhook has a hook slot concealed on the distal end. A perforating suture hook is used to pierce the rotator cuff and to pass suture through the rotator cuff and into position for retrieval by the hook slot, which is activated after drilling the tunnel to pull the suture through tunnel. The rotator cuff is held taut and in position by a retaining suture.

6 Claims, 8 Drawing Sheets

METHOD AND APPARATUS FOR ARTHROSCOPIC ROTATOR CUFF REPAIR UTILIZING BONE TUNNELS FOR SUTURE ATTACHMENT

BACKGROUND OF THE INVENTION

1. Field of the Invention

The invention relates to a drill guide and method for arthroscopic surgery, and more specifically to a drill guide and method for arthroscopic rotator cuff repair.

2. Discussion of the Related Art

The majority of tissue repair to the shoulder area, such as rotator cuff repair involving reattaching torn rotator cuff tendons to bone, is currently performed as an "open" procedure. A less-invasive arthroscopic procedure is preferable because the smaller incision leads to a decreased chance of morbidity, reduces post-operative pain and scarring, and generally shortens recovery times. Open procedures have been necessary due to the relatively small working space available within the shoulder capsule, and the lack of procedure-specific instrumentation to complete a successful rotator cuff repair arthroscopically.

Recently, arthroscopic methods of shoulder surgery using "suture anchors" have been introduced and adapted to the repair of the rotator cuff. See, e.g., "The Revo Rotator Cuff Fixation System", Linvatec Corp. (1993), a surgical technique described by Stephen J. Snyder, M.D., Southern California Orthopedic Institute. See also U.S. patent application Ser. No. 08/288,228, filed Aug. 26, 1994, now U.S. Pat. No. 5,575,801, the disclosure of which is incorporated herein by reference.

Various styles, sizes and methods of suture anchors have been developed. The known suture anchors are manufactured from various materials, including biocompatible metal and plastics. The anchors also can be biodegradable or resorbable. Suture anchors typically are implanted into the bone with suture attached to the anchor. Various techniques of suture attachment have been developed.

Surgical methods utilizing suture anchors are disadvantageous because they often do not allow good tendon-to-bone contact. Suture breakage and insufficient pull-out strength are also major disadvantages of metal anchor implants.

When suture breakage occurs during anchor insertion or knot tying, the anchor must be abandoned and another used alongside the failed original. This adds yet another metallic foreign body that can cause soft tissue damage. Additional expense is also incurred.

When suture anchors pull out, foreign bodies are left in the body to do additional damage by abrasion or migration to remote sites. Metallic foreign bodies have been reported to cause vessel injury, and even death by migration to the heart and lungs.

Thus, the need exists for an apparatus and method for arthroscopic rotator cuff repair which does not leave metallic foreign bodies within the patient's shoulder capsule. The instrumentation must work effectively, within the small confines of the shoulder, to create small diameter holes that form a natural bone bridge, perforating the damaged rotator cuff with suture, and holding the rotator cuff securely in place until the ligaments naturally reattach to the bone.

Additionally, of great concern in arthroscopic surgery of the shoulder is the axillary nerve, which travels transversely on the undersurface of the deltoid, approximately 5 cm. distal to the edge of the acromion. Until now, all "safe" portals for shoulder arthroscopy have been proximal to the level of the axillary nerve; thus, the need exists for a technique that allows safe introduction of arthroscopic instruments to the shoulder, such as inserting the drill-hook guide distal to the axillary nerve.

SUMMARY OF THE INVENTION

The present invention overcomes the deficiencies of the prior art noted above by providing a drillhook guide system having a cannulated shaft, and an aiming arm arranged slidably on the cannulated shaft.

The invention further includes a drillhook for insertion within the cannulated shaft of the drillhook guide system. The drillhook is a thin-walled tube, with a drill shank provided inside the tube. The drill shank has a drill bit point and a hook slot located proximal to the drill point. Advantageously, the drill shank is slidable within the tube selectively to expose the hook slot outside the distal end of the tube. The drill shank is prevented from rotating within the tube when the drillhook is used as a bit for drilling. The drill shank preferably is spring biased to slide away from the distal end of the tube. Preferably, an activator is used selectively to expose the hook slot outside the distal end of the tube.

The aiming arm slides with respect to the cannulated shaft along an axis parallel to the central axis of the cannulated shaft. Preferably, the aiming arm is lockable in selected positions along the shaft. The aiming arm has a radiused distal end for marking an exit point for the drillhook. The radiused portion allows the distal end to clear the projection of the greater tuberosity.

The cannulated shaft preferably has an acute angle formed on its distal end. The angle allows the guide to lie approximately flush along the proximal humerus. Advantageously, the drillhook guide system has spikes formed on a distal end thereof for stabilizing the guide system during drillhook insertion. Preferably, the shaft is calibrated to show drilling depth.

A perforating suture passer is used in conjunction with the drillhook guide system according to a preferred embodiment of the invention. The perforating suture passer includes a hypodermic tube having a needle tip. A flexible rod is inserted within the tube. A non-abrasive, wire loop is attached to the distal end of the flexible rod. The flexible rod passes the wire loop through the hypodermic tube and outside the distal end of the hypodermic tube. The function of the wire loop is to thread suture through the suture passer.

The end of the hypodermic tube preferably terminates in a 70° arc for accessing the subacromial space and piercing the rotator cuff. The length of the flexible rod is such that the wire loop can pass at least 5 mm. beyond the distal end of the hypodermic tube. The suture passer also includes a cannulated handle attached to the hypodermic tube. A countersink preferably is formed on the proximal end of the handle to facilitate insertion of the wire loop and flexible rod.

A cylindrical handle attached to the flexible rod assists passing the flexible rod through the hypodermic tube. Advantageously, the cylindrical handle has a flat portion formed on it that is aligned parallel with a plane containing the wire loop.

The present invention also relates to a method of arthroscopic rotator cuff repair utilizing the apparatus described above. The method involves forming a bone tunnel through the proximal humerus with the drillhook using the drillhook guide, passing suture through the damaged rotator cuff using the perforating suture passer, passing the suture through the tunnel using the hook slot on the drillhook, and tying off the suture. The method preferably includes holding the rotator cuff taut and in place using a traction suture. After surgery, the bone tunnels fill back in by osteogenesis, and the shoulder is eventually returned to its original state of wellness.

The method of arthroscopic rotator cuff repair preferably includes forming an anterior-inferior portal, located distal to the axillary nerve, for safe introduction of the drill-hook guide at a location distal to the axillary nerve.

Other features and advantages of the present invention will become apparent from the following description of the invention which refers to the accompanying drawings.

DETAILED DESCRIPTION OF THE PREFERRED EMBODIMENTS

Figure 1:
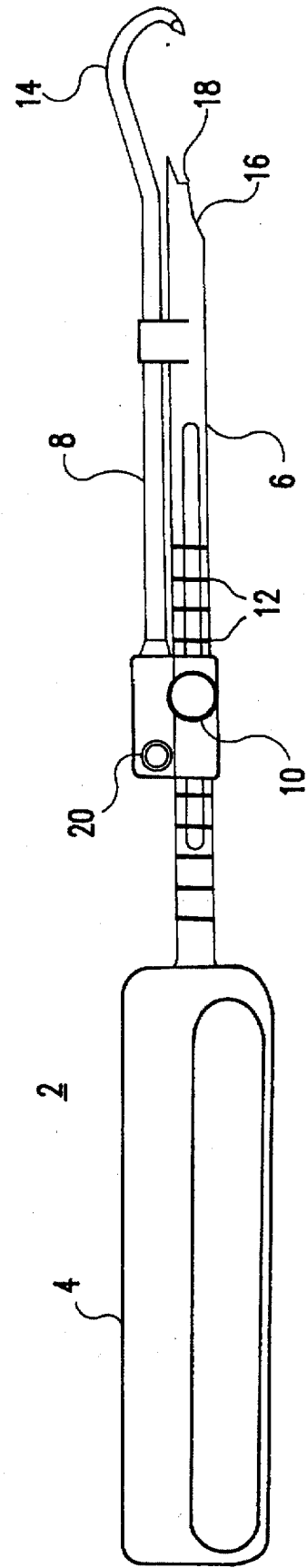
FIG. 1 is a side view showing a drillhook guide according to a preferred embodiment of the present invention.

Referring first to FIG. 1, a drillhook guide 2 according to a preferred embodiment of the present invention is shown. The guide has a cannulated handle 4 and shaft 6, and an adjustable aiming arm 8 that is slidable along shaft 6. A thumb screw 10 can be tightened to lock aiming arm 8 in place once the desired location and length of the bone tunnel have been determined. Markings 12 on the central shaft of the guide are calibrated to indicate the derived tunnel length at any given adjustment.

As described in detail below, aiming arm 8 of drillhook guide 2 is provided with a distal end 14 which is radiused to mark an exit point of a drillhook inserted through cannulated shaft 6 and drilled through bone tissue. The distal end of cannulated shaft 6 is provided with a face 16 cut at an acute angle to allow close approximation of the drillhook guide to the surface of the bone to be drilled. Perpendicular spikes 18 are provided on the leading edge of cannulated shaft 6 to assist in stabilizing the guide during drillhook insertion.

Figure 2:
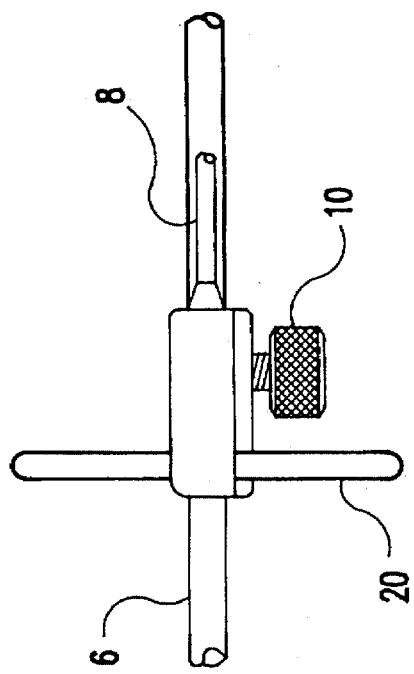
FIG. 2 is a sectional top view detailing the drillhook guide of FIG. 1.

Referring to FIG. 2, a segmented top view of a midsection of drillhook guide 2 shows a proximal end of aiming arm 8 in greater detail. A cross bar 20 facilitates manipulation of the drillhook guide and aiming arm 8. Knurled thumb screw 10 locks aiming arm 8 in place along cannulated shaft 6.

Figure 4:
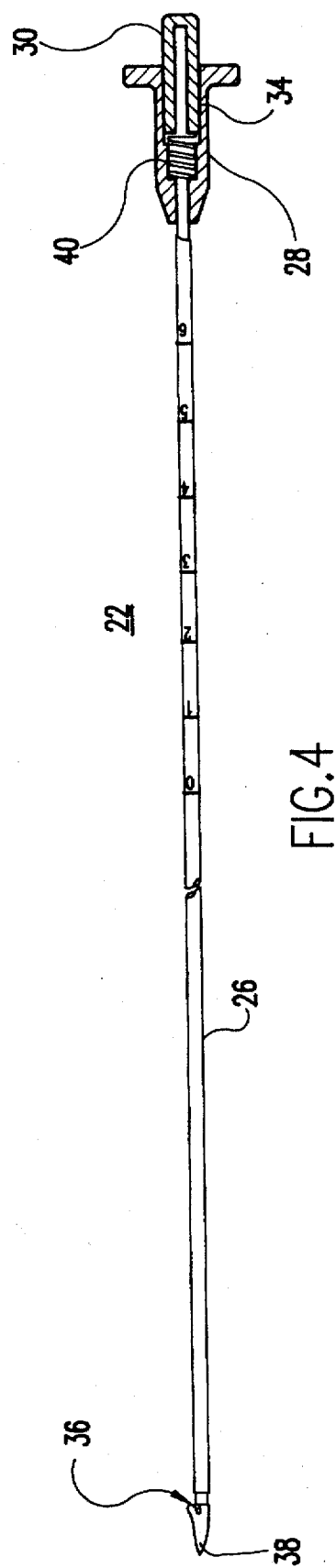
FIG. 4 is a cut away side view of the drill hook of FIG. 3.
Figure 3:
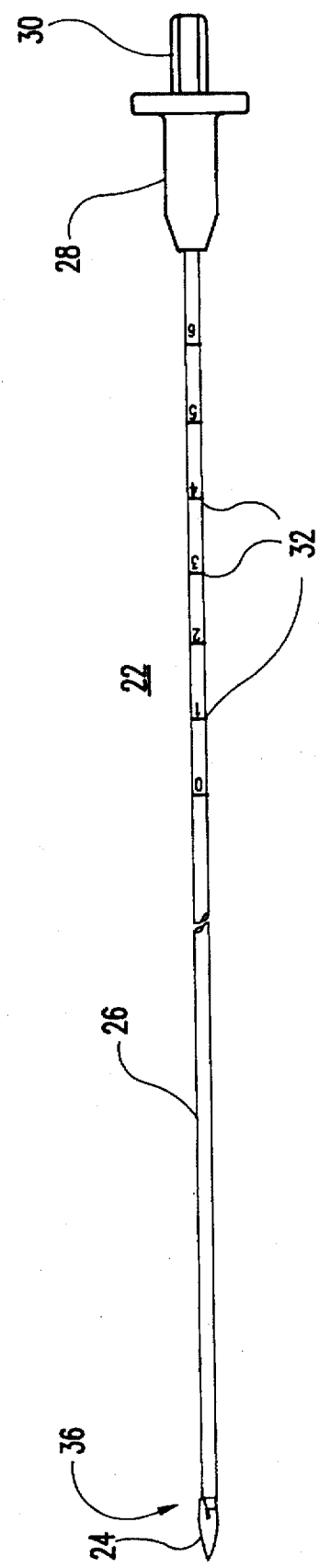
FIG. 3 is a side view showing a drill hook showing a preferred embodiment of the present invention.

Referring to FIGS. 3 and 4, a drillhook 22 according to a preferred embodiment of the present invention is shown. Drillhook 22 is a multi-functional mechanism. A trocar pointed drill shank 24 is enclosed within a thin-walled tube 26. Tube 26 is housed within a cylindrical base 28 that also acts as a stop for a spring loaded hexagonal activator 30. Calibrated markings 32 on tube 26 indicate the depth to which drillhook 22 has been drilled into bone.

Hexagonal activator 30 is matched with a hexagonal bore 34 (FIG. 4) of cylindrical base 28 for anti-rotation stability while drillhook 22 is driven through the tissue into bone using a motorized drill attached to hexagonal activator 30. Once a desired bone-tunnel depth has been achieved, the motorized drill is removed and hexagonal activator 30 is depressed, exposing a crochet hook-style slot 36 located at trocar-pointed tip 38, as described further below.

Referring again to FIG. 4, drillhook 22 is shown in an open position, with hook slot 36 fully exposed outside the end of tube 26. A spring 40, captured within cylindrical base 28, urges trocar-pointed drill shank 24, captured within hexagonal activator 30 away from the distal end of tube 26. Hook slot 36 is concealed inside tube 26 (see FIG. 3) when drillhook 22 is not being activated by activator 30.

Figure 5:
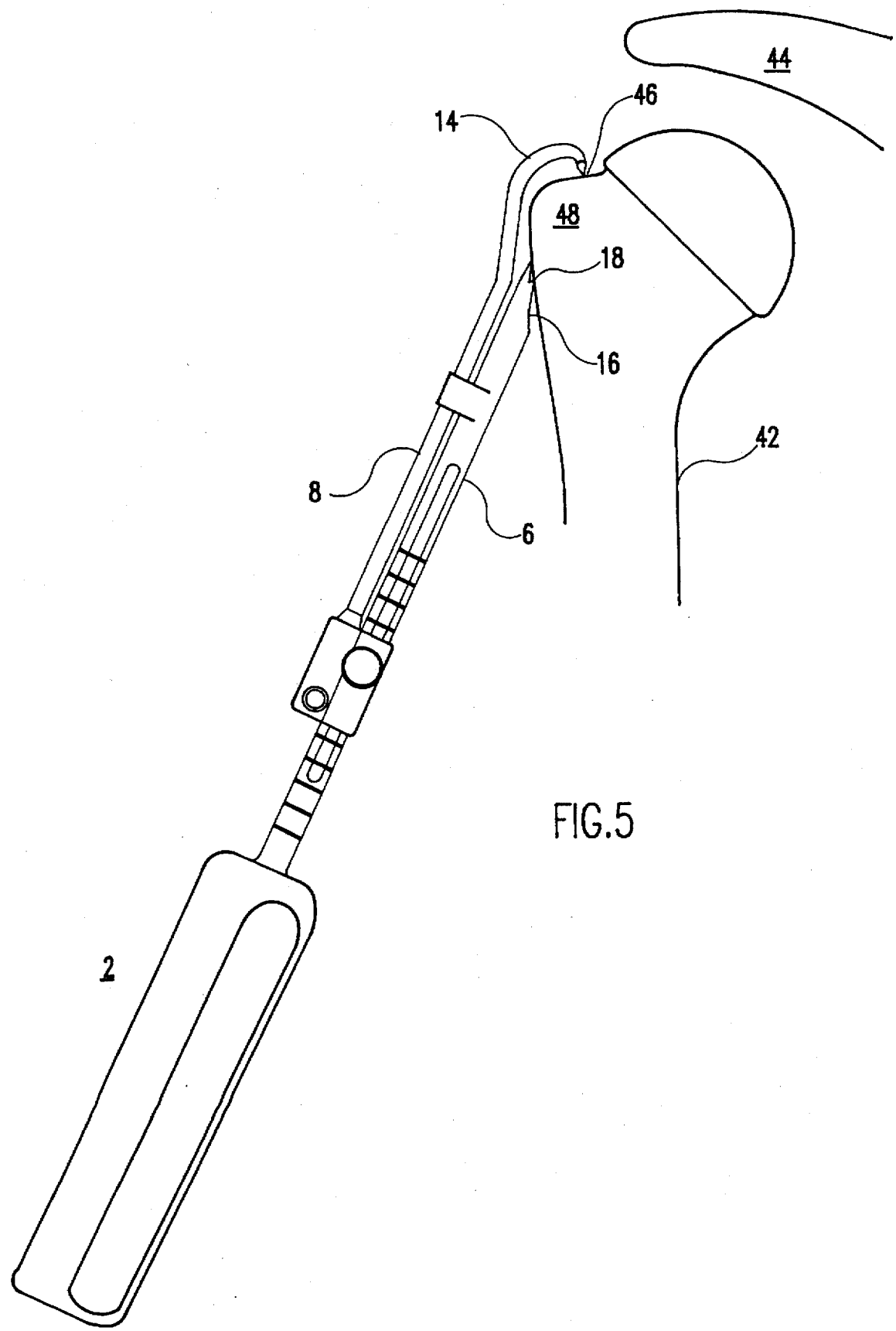
FIG. 5 is a side view of the drillhook guide of FIG. 1 shown schematically in position along the proximal humerus.

Referring to FIG. 5, drillhook guide 2 is shown schematically in place along the proximal humerus 42 in relative location to acromion 44. Radiused distal end 14 of aiming arm e of drillhook guide 2 is shown marking the exit point 46 of drillhook 22 and clearing the projection of the greater tuberosity 48. Face 16, cut at an acute angle on the distal end of cannulated shaft 6, allows a close approximation to the surface of the humerus, so that the end of the drill guide is flush to the bone at the time of creating the bone tunnel. Perpendicular spikes 18 on the leading edge of cannulated shaft 6 assist in stabilizing guide 2 during drillhook insertion.

Figure 6:
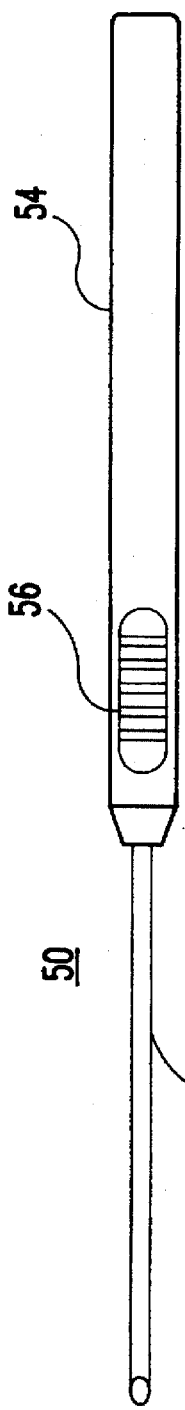
FIG. 6 is a top view showing a perforating suture passer according to a preferred embodiment of the present invention.

Referring to FIG. 6, a perforating suture passer 50 according to a preferred embodiment of the present invention is shown. A regular wall hypodermic tube 52 is contained within a cannulated, cylindrical handle 54. Handle 54 preferably has a recessed and ribbed area 56 providing a non-slip gripping section.

Figure 7:
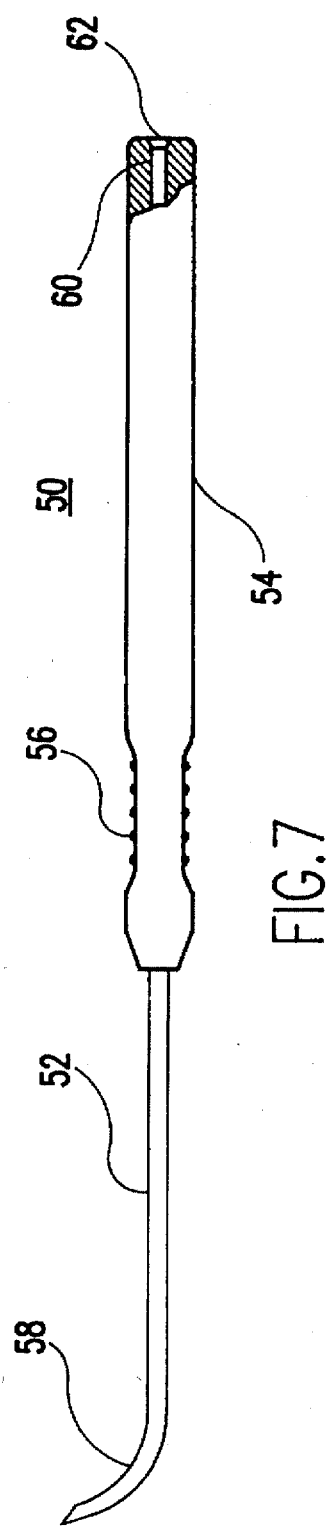
FIG. 7 is a side view of the perforating suture passer of FIG. 6.

Referring to FIG. 7, large radius 58 on the distal end of perforating suture passer 50 is shown. Radius 58 terminates in 70° of arc to assist a physician using the suture passer in accessing the relatively small confines of the subacromial space, and then piercing the rotator cuff. FIG. 7 also shows in a sectional view cannula 60 of handle 54. Preferably, a countersink 62 is formed in the proximal end of handle 54 which facilitates leading in a flexible wire loop, as discussed below.

Figure 8:
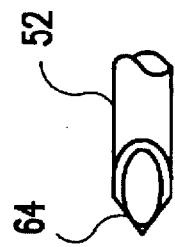
FIG. 8 is a sectional detail of the perforating suture passer of FIGS. 6 and 7.

Referring to FIG. 8, the distal end of hypodermic tube 52 is shown in enlarged detail illustrating the needle tip 64 facilitating passage of tube 52 through the tendinous tissue of the rotator cuff bands.

Figure 9:
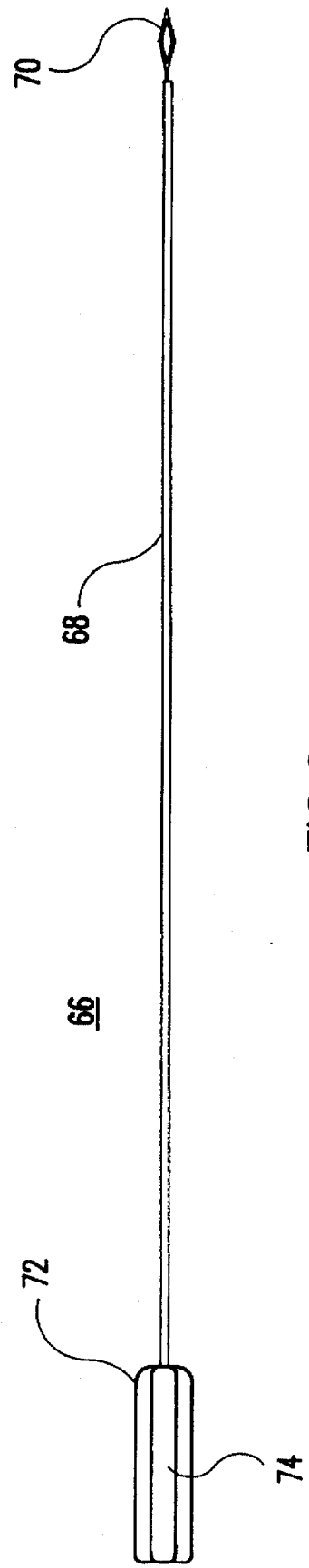
FIG. 9 is a side view showing a flexible rod and wire loop according to a preferred embodiment of the present invention.

Referring to FIG. 9, a flexible wire loop 66 according to a preferred embodiment of the present invention is shown. A small diameter rod 68 preferably is made of an extremely flexible material, such as Nitinol or other suitable wire. A nonabrasive closed loop 70 is swaged or otherwise attached to the distal end of flexible rod 68. Loop 70 is capable of transporting suture of various diameters and compositions through the lumen of perforating suture passer 50 without suture breakage. The flexible shaft preferably is of sufficient length to pass the suture at least 5 mm. past the distal end of perforating suture passer 50.

The proximal end of flexible wire loop 66 has a cylindrical handle 72 that is used to safely advance loop 70 and suture through perforating suture passer 50. A flat 74 is milled on handle 72 in line with loop 70 as an external indication of loop orientation.

Figure 10:
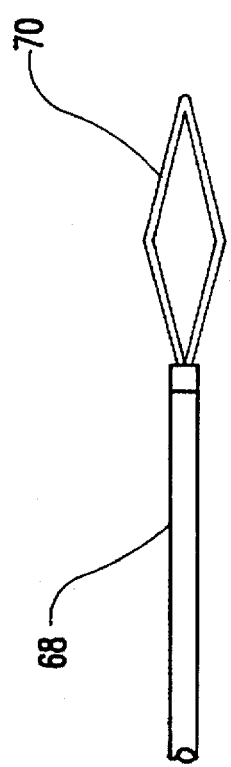
FIG. 10 is a sectional detail of the flexible rod and wire loop of FIG. 9.

Referring to FIG. 10, an enlarged detail of loop 70 is shown. Although a trapezoidal loop is shown, any configuration of loop is acceptable as long as an open passageway for the suture can be maintained during the time the loop is inside the shoulder capsule.

Figure 11:
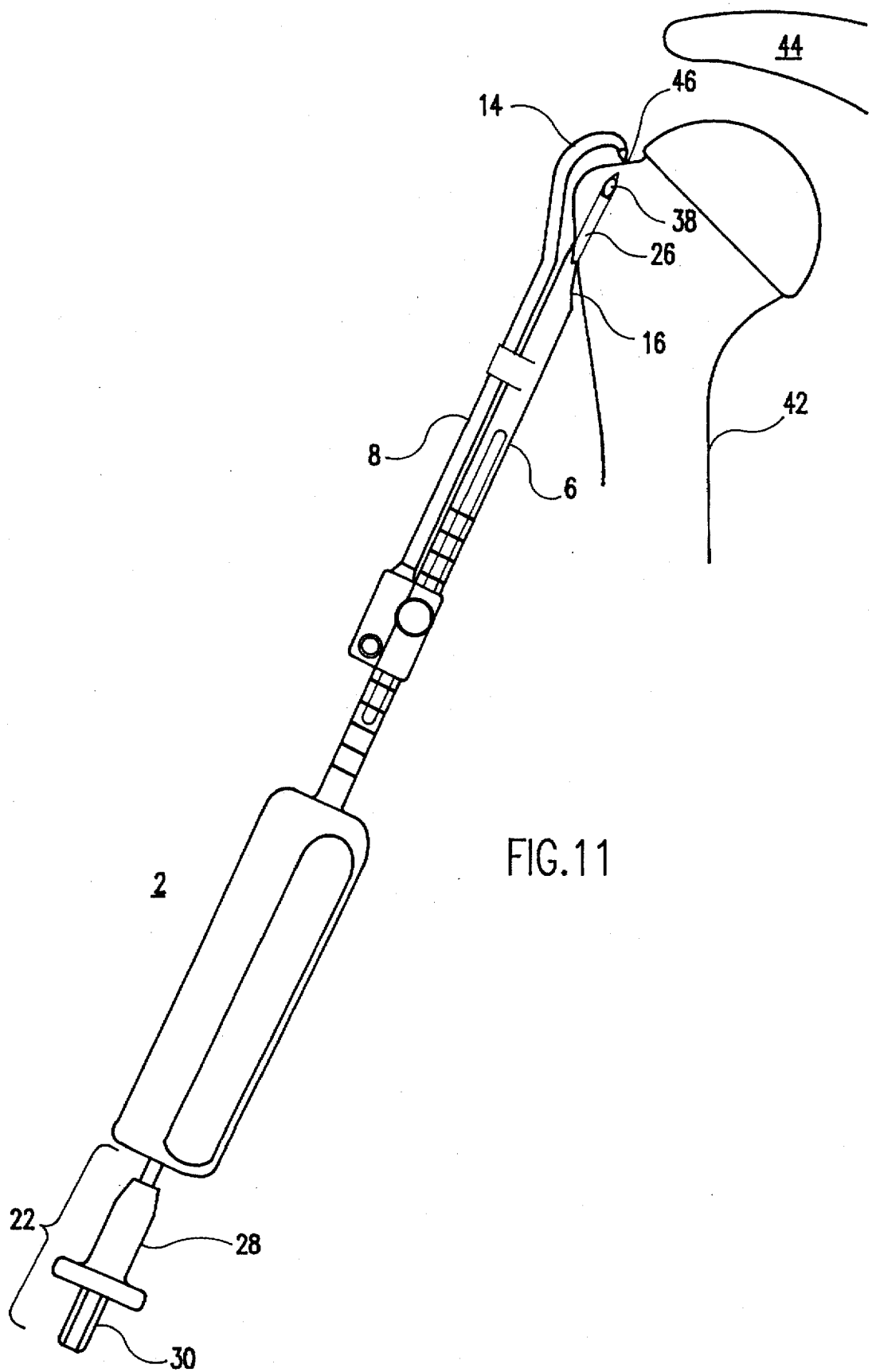
FIG. 11 is a schematic view of the present invention illustrating various steps in a method of arthroscopic rotator cuff repair according to a preferred embodiment of the present invention.
Figure 12:
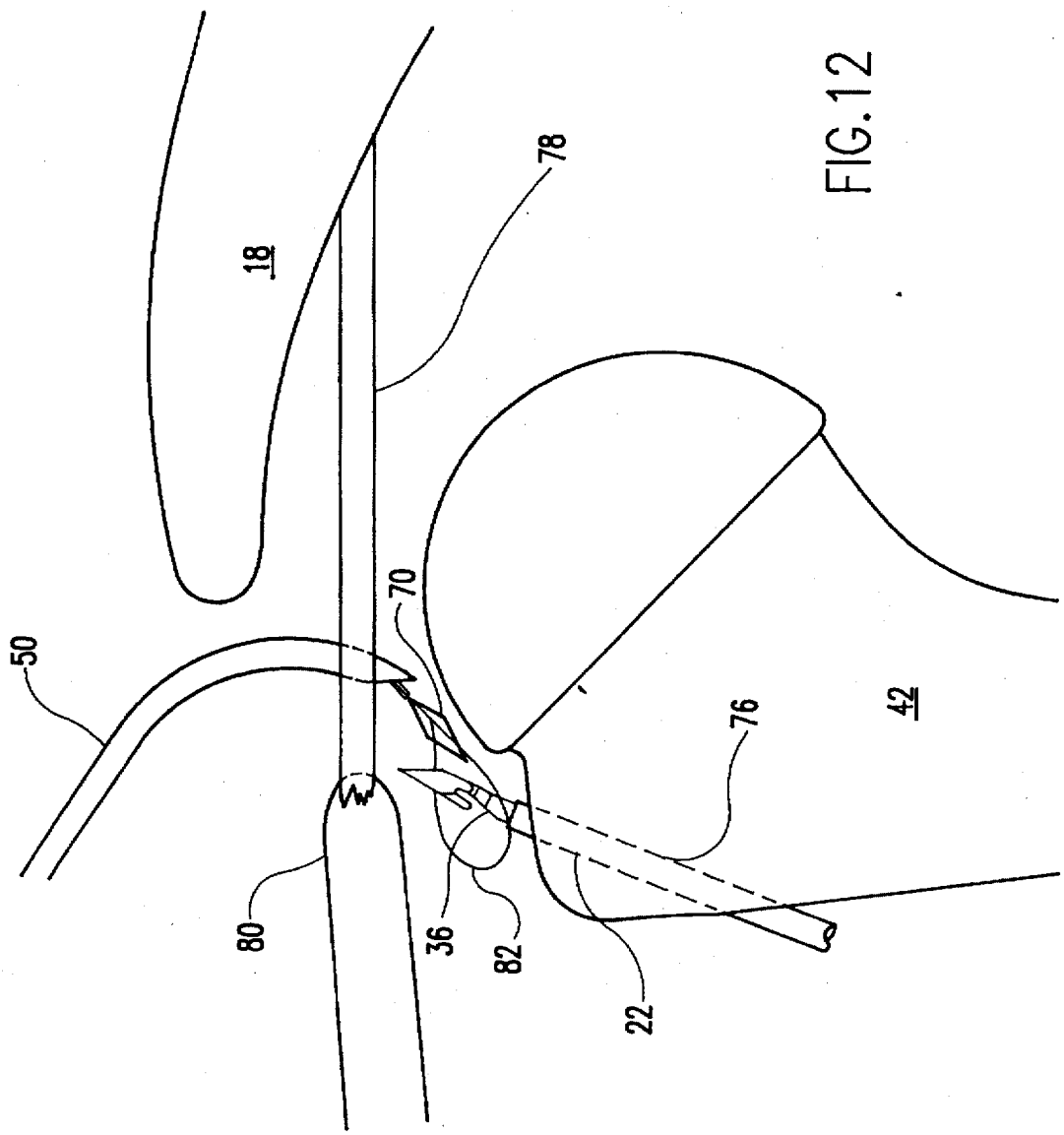
FIG. 12 is schematic illustration showing further steps in the method of arthroscopic rotator cuff repair shown in FIG. 11 according to a preferred embodiment of the present invention.

Referring to FIGS. 11 and 12, a method of arthroscopic rotator cuff repair according to a preferred embodiment of the present invention is shown. FIG. 11 illustrates schematically drill guide 2 in place along proximal humerus 42. For clarity, the drill guide is shown magnified with respect to the bone. Drillhook 22 is inserted within drill guide 2. Hexagonal activator 30 is connected to a motorized drill (not shown) for drilling purposes. Trocar point 38 extends beyond the distal end of cannulated shaft 6, having been drilled part way into humerus 42. Hook slot 36 is not shown in FIG. 11, being concealed within tube 26.

As noted above with respect to FIG. 5, radiused distal end 14 of aiming arm 8 is shown marking the expected exit point 46 of drillhook 22 and clearing the projection of the greater tuberosity 48. Face 16 cut at an acute angle on the distal end of cannulated shaft 6 allows a close approximation to the surface of the humerus so as to be flush against the shoulder bone at the time of creating the bone tunnel. Perpendicular spikes 18 on the leading edge of cannulated shaft 6 are pressed against the bone to assist in stabilizing guide 2 during drillhook 22 insertion.

Referring to FIG. 12, further steps of the surgical method according to a preferred embodiment of the present invention are shown. Drillhook 22 is inserted through the greater tuberosity of proximal humerus 42. Drilling of bone tunnel 76 with drillhook 22 is complete. Hexagonal activator 30 has been depressed to place drillhook 22 in the open position, exposing hook slot 36.

Rotator cuff 76 is held taut and in place by means of a traction suture 80. Perforating suture passer 50 has pierced through rotator cuff 76, and wire loop 70 with suture loop 82 is around hook slot 36 of drillhook 22 and about to be pulled down and through bone tunnel 76. Alternatively, suture passer 50 can pierce through the rotator cuff from inferior to superior.

The following is a detailed description of a surgical procedure according to preferred embodiment of the present invention of arthroscopic rotator cuff repair utilizing the instruments of the present invention, including the drillhook guide, drillhook and perforating suture passer with flexible wire loop:

1. At least three incision portals are created in the shoulder to perform this procedure. One portal is for arthroscope insertion. The standard posterior location that is commonly prescribed for use with a 30° arthroscope also is satisfactory for auxiliary instrument insertion. A second posterior puncture style incision is made for inflow and instrumentation. The second portal is used for introduction of instruments and to accommodate the positioning of the rotator cuff with the traction sutures. A third incision is for the positioning of drillhook guide system 2, as well as for other instrumentation and placement of traction sutures. The third incision should be made central to the longitudinal axis of humerus 42, beginning 3 cm. distal to the superior aspect of the greater tuberosity and traversing distally substantially 1½ cm.

Figure 13:
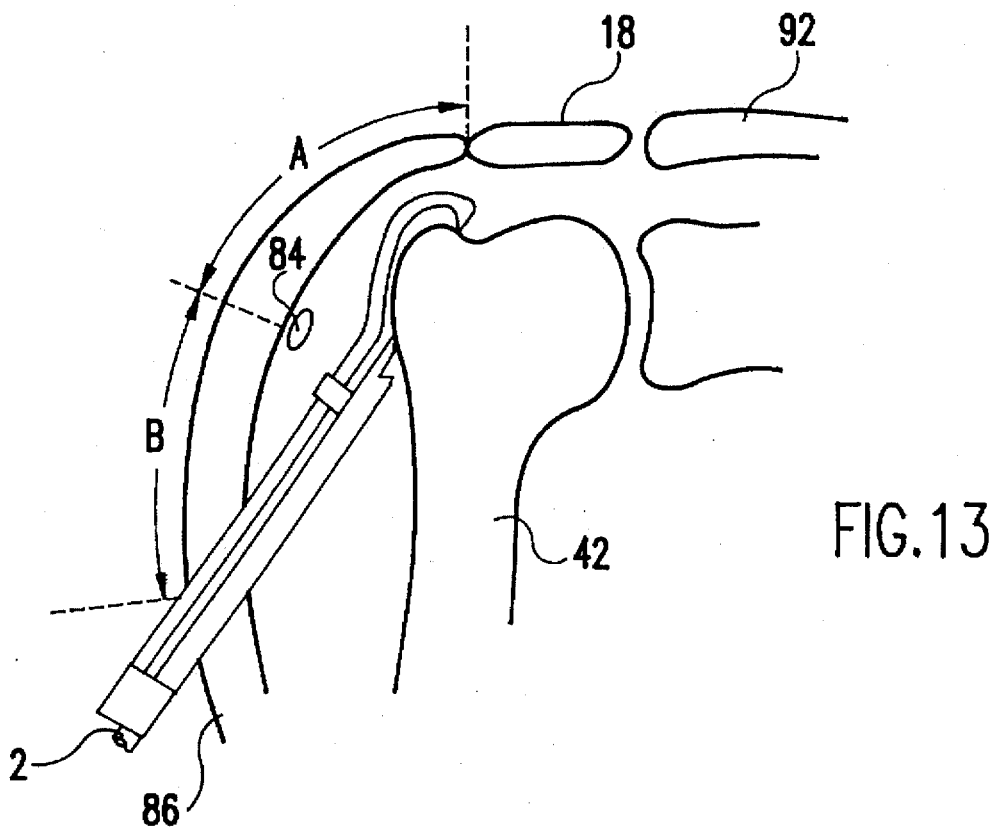
FIG. 13 is a schematic view showing the drill guide in position in a shoulder indicating the location of the axillary nerve according to a preferred embodiment of the present invention.

A preferred embodiment uses a fourth, anterior-inferior (sub-axillary nerve) portal. Referring to FIG. 13, axillary nerve 84 travels transversely on the undersurface of deltoid 86, approximately 5 cm. distal (distance "A") to the edge of acromion 18. Drillguide 2 is shown inserted through the portal formed approximately 5 cm. (distance "B") distal of the axillary nerve location, a total of approximately 10 cm. from the acromial edge.

Figure 14:
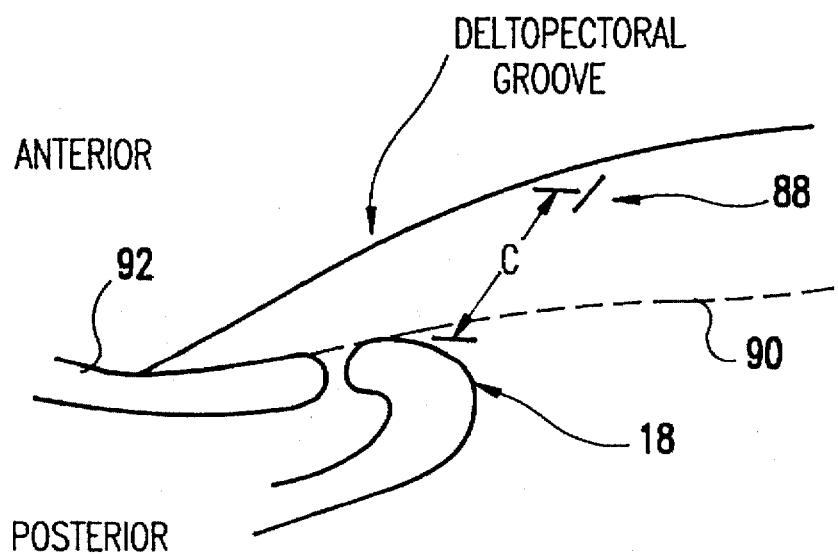
FIG. 14 is a schematic view of a portion of the right shoulder viewed from above showing the location of the anterior-inferior portal according to a preferred embodiment of the surgical method of the present invention.

Referring to FIG. 14, an anterior-inferior portal 88 is formed at a position distal to axillary nerve 84 to allow safe introduction of the drill-hook guide distal to axillary nerve 84. Portal 88 preferably is a 1 cm. longitudinal puncture located approximately 10 to 12 cm. (distance "C") distal to the anterolateral edge of acromion 18, and situated anterior to a projected anterior clavicular line 90 of the anterior border of clavicle 92.

After the suture has been passed through bone tunnel 76 and out anterior-inferior portal 88, a knot pusher is threaded over the suture and passed through the anterior-inferior portal, going immediately to bone with the knot pusher, and then "walking" the knot pusher proximally to the subacromial space for tying. In this way, the drill-hook is introduced safely through anterior-inferior portal 88 distal to axillary nerve 84, and the suture is safely delivered through anterior-inferior portal 88 to the subacromial space by passing the suture distal to the nerve.

2. Bleeding bone should be exposed on the superior surface of the greater tuberosity 48.

3. An optional traction suture or sutures 80 are placed on the lateral edge of torn rotator cuff 78 in the following manner: A #2 braided suture is pre-loaded within flexible wire loop 66. Rotator cuff 78 is grasped and kept taut. The rotator cuff is perforated from superior to inferior using perforating suture passer 50.

The wire loop is advanced until the #2 braided suture can be seen. One limb of the suture is retrieved from under the rotator cuff and then the perforating suture passer is removed along with the second limb of the traction suture. This step is repeated as many times as is necessary to safely manipulate the cuff. Alternatively, the suture may be passed from inferior to superior with perforating suture passer 50, then threaded into drillhook 22.

4. Entering the joint capsule using the same portal through which the traction sutures were placed, rotator cuff 78 is perforated once again with suture passer 50 pre-loaded with suture. Flexible wire loop 66 is advanced as far as possible, then retracted to the end of suture passer 50, leaving a suture "lasso" under the rotator cuff.

5. Adjustable aiming arm 8 of the drillhook guide system 2 is advanced to its longest position. The distal end of guide system 2 is inserted into the 1½ cm. distal incision. Following the contour of the proximal humerus, the tip of aiming arm 8 is placed in the area of the abraded bleeding bone (created in step 2 above) at the desired exit point of drillhook 22 Keeping the exit point fixed, the instrument is pushed into the incision until perpendicular spikes 18 on the distal end of cannulated shaft 6 are firmly fixed on the cortical bone surface.

6. Once the drillhook guide is firmly in position, thumb screw 10 on the side of adjustable aiming arm 8 is tightened, locking the instrument in position. Calibrated markings 12 on cannulated shaft 6 indicate the bone tunnel length at the selected setting.

7. A power drill with a Jacobs chuck, for example, is set up with drillhook 22 secured in the chuck. Hexagonal activator 30 is inserted fully into the chuck up to cylindrical base 28. Trocar point 38 of drillhook 22 is introduced into the handle 4 of the drill guide system, and advanced until the trocar point comes into contact with bone. Bone tunnel 76 is formed by applying power to the drill and advancing drillhook 22 through bone until calibrated markings 32 on the drillhook equal the tunnel length that had been established from the drillhook guide system. Once the tunnel is complete, the power drill is removed from the drillhook.

8. The crochet hook-style slot 36 of the drillhook is exposed by depressing hexagonal activator 30 on the distal end of the drillhook. Internal manipulation of the suture "lasso" is performed to bring the lasso over the end of drillhook 22 and to capture the lasso by releasing spring-loaded activator 30.

9. One limb of the suture is pulled down and out of bone tunnel 76 with the removal of drillhook 22 and the other suture limb is pulled out of the shoulder with the extraction of perforating suture passer 50.

10. Steps 5 through 9 are repeated as many times as necessary to assure secure fixation of the damaged rotator cuff. Suture is secured using a knot pusher that is threaded over the distal suture limb outside the anterior-inferior portal. The knot pusher then is inserted through the anterior-inferior portal to bone, where it is "walked" proximally along the bone to the greater tuberosity, thereby delivering the suture to the subacromial space where it can be retrieved and tied through another portal.

11. Traction can now be placed and maintained on the cuff while positioning the tissues in the proper location of repair. Either simple or mattress suture knot configurations can be used to reattach the damaged rotator cuff in its original anatomical position.

A preferred technique of knot-tying is with a double-diameter knot pusher, the subject of co-pending U.S. patent application OFGS File No. P/1493-89, the entire disclosure of which is incorporated herein by reference. Using the double-diameter knot pusher, the first throw of the suture can be held tightly against the bone. The inner-diameter portion holds the first throw of the knot while the second throw of the knot is pushed down with the outer-diameter portion of the knot pusher.

Although the present invention has been described in relation to particular embodiments thereof, many other variations and modifications and other uses will become apparent to those skilled in the art. The present invention is to be limited not by the specific disclosure herein, but only by the appended claims.

What is claimed is:

1. A method of arthroscopic rotator cuff repair, comprising the steps of:

forming a bone tunnel through the proximal humerus with a drillhook using a drillhook guide system, the drillhook including a drill shank having a hook slot, the guide system having a cannulated shaft with an aiming arm slidably disposed on the cannulated shaft;

passing suture through the damaged rotator cuff;

passing the suture through the tunnel by retrieving the suture using the hook slot; and tying off the suture.

2. The method of arthroscopic rotator cuff repair according to claim 1, wherein the drill shank is slidably disposed within a tube having a distal end, the hook slot being selectively exposable outside the distal end of the tube, and the step of passing suture through the tunnel further comprises exposing the hook slot on the drillhook outside the distal end of the tube.

3. The method of arthroscopic rotator cuff repair according to claim 1, wherein the step of passing suture through the damaged rotator cuff comprises the steps of:

guiding the suture using a suture passer having a point; and piercing the rotator cuff with the point of the suture passer.

4. The method of arthroscopic rotator cuff repair according to claim 1, further comprising the step of holding the rotator cuff taut and in place.

5. The method of arthroscopic rotator cuff repair according to claim 4, wherein the rotator cuff is held taut and in place using a traction suture.

6. The method of arthroscopic rotator cuff repair according to claim 1, further comprising the step of forming an anterior-inferior portal located distal to the axillary nerve for safe introduction of the drill-hook guide at a location distal to the axillary nerve.

\* \* \* \* \*